US00PP35279P3

(12) United States Plant Patent
Werner et al.

(10) Patent No.: US PP35,279 P3
(45) Date of Patent: Jul. 25, 2023

(54) ***CERCIS* PLANT NAMED 'NC2017-6'**

(50) Latin Name: *Cercis canadensis*
Varietal Denomination: NC2017-6

(71) Applicant: North Carolina State University, Raleigh, NC (US)

(72) Inventors: Dennis Werner, Raleigh, NC (US); Leanne M. Kenealy, Durham, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/968,097

(22) Filed: Oct. 18, 2022

(65) Prior Publication Data

US 2023/0125067 P1 Apr. 20, 2023

Related U.S. Application Data

(60) Provisional application No. 63/257,253, filed on Oct. 19, 2021.

(51) Int. Cl.
*A01H 6/54* (2018.01)
*A01H 5/00* (2018.01)
*A01H 6/00* (2018.01)

(52) U.S. Cl.
USPC ..... Plt./216
CPC ..... *A01H 6/00* (2018.05)

(58) Field of Classification Search
USPC ..... Plt./216
CPC ..... A01H 6/54; A01H 5/00
See application file for complete search history.

(56) References Cited

U.S. PATENT DOCUMENTS

PP17,161 P3 10/2006 Woody
PP22,097 P3 8/2011 Werner

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Cercis* plant, referred to by its cultivar name 'NC2017-6', is disclosed. The new cultivar originated in a controlled breeding program. Plants of the new variety produce small and purple-colored foliage. The new variety is moderately vigorous. Plants of the new variety exhibit a highly branched, and compact growth habit.

2 Drawing Sheets

Latin name of genus and species of plant claimed: *Cercis canadensis.*

Variety denomination: 'NC2017-6'.

BACKGROUND OF THE INVENTION

The present invention relates to a new and distinct cultivar of *Cercis* plant botanically known as *Cercis canadensis* and hereinafter referred to by the cultivar name 'NC2017-6'.

The new cultivar originated in a controlled breeding program in Jackson Springs, N.C. in March 2011.

The new *Cercis* cultivar is the result of a controlled cross wherein two parents were crossed which previously had been studied in the hope that they would contribute the desired characteristics. The female parent (i.e., the seed parent) of the new cultivar is *Cercis* 'Ruby Falls', U.S. Plant Pat. No. 22,097. The male parent (i.e., the pollen parent) of the new cultivar is *Cercis* 'Ace of Hearts', U.S. Plant Pat. No. 17,161.

The parentage of the new variety can be summarized as follows:

'Ruby Falls' x 'Ace of Hearts'

The seeds resulting from the above pollination were sown and small plants were obtained which were physically and biologically different from each other. Selective study in 2017 in a controlled environment in Willow Spring, N.C. resulted in the identification of a single plant of the new variety, which was selected for its reduced leaf size, highly branched compact growth habit, and purple-colored foliage.

Asexual reproduction of the new cultivar by chip budding since August 2016 in Belvidere, Tenn. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'NC2017-6' as a new and distinct cultivar of *Cercis* plant:

(a) Small and purple-colored foliage; and
(b) Moderately vigorous, highly branched and compact growth habit.

The new variety of the present invention can readily be distinguished from its ancestors. More specifically, plants of 'Ruby Falls' (i.e., the seed parent) exhibit a weeping habit, whereas plants of the new variety exhibit a non-weeping and compact growth habit. In addition, plants of 'Ace of hearts' (i.e., the pollen parent) display green-colored foliage, whereas plants of the new variety display purple-colored foliage.

Moreover, the new variety can be readily distinguished from other similar non-parental varieties. Of the many commercially available *Cercis* cultivars, the most similar in comparison to the new cultivar is 'Forest Pansy', (not patented). However, plants of the new cultivar differ from plants of 'Forest Pansy' in at least the following characteristic:

1. Plants of the new cultivar have a more highly branched architecture and compact growth habit than plants of 'Forest Pansy'; and
2. Plants of the new cultivar have a darker purple foliage color than plants of 'Forest Pansy'.

BRIEF DESCRIPTION OF THE PHOTOGRAPHS

The accompanying photographs show, as nearly true as it is reasonably possible to make the same in color illustrations of this type typical growth habit and foliage characteristics of the new cultivar. Colors in the photographs differ slightly from the color values cited in the detailed description, which accurately describes the colors of 'NC2017-6'. The plants were five years of age and growing in the ground in Cochranville, Pa. in 2021.

DETAILED BOTANICAL DESCRIPTION

Figure 1:
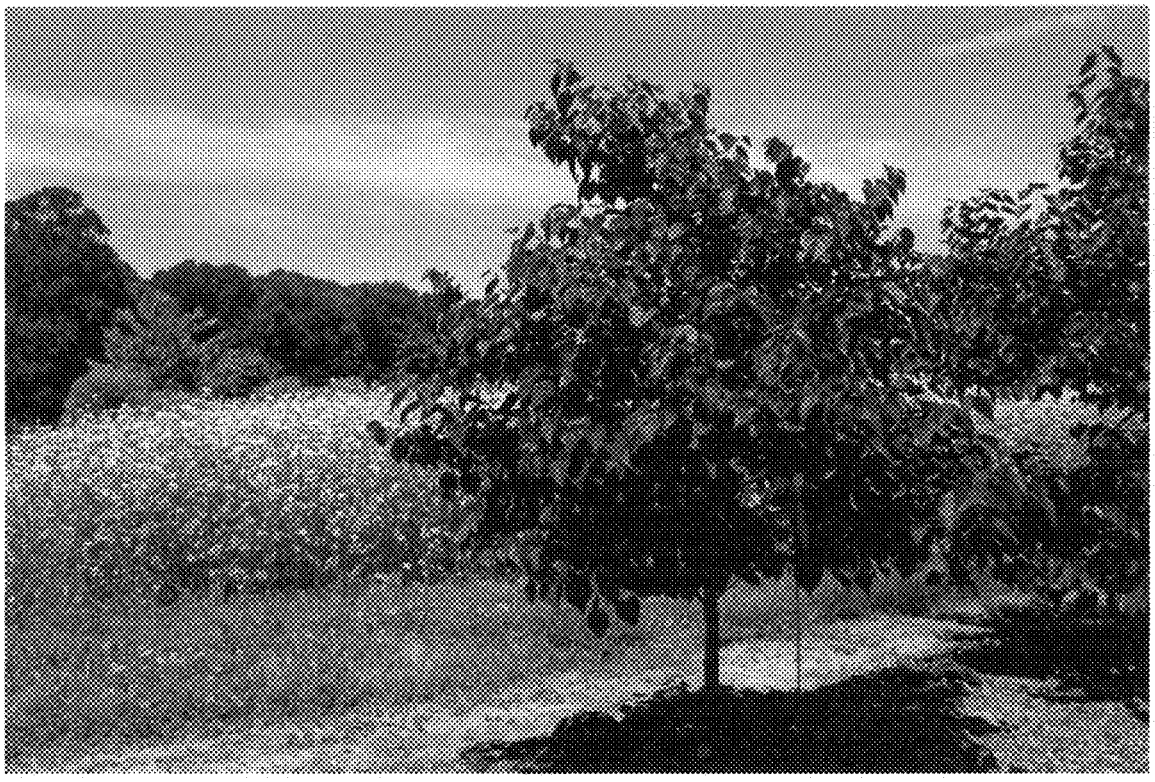
FIG. 1 illustrates a side view of 'NC2017-6'
Figure 2:
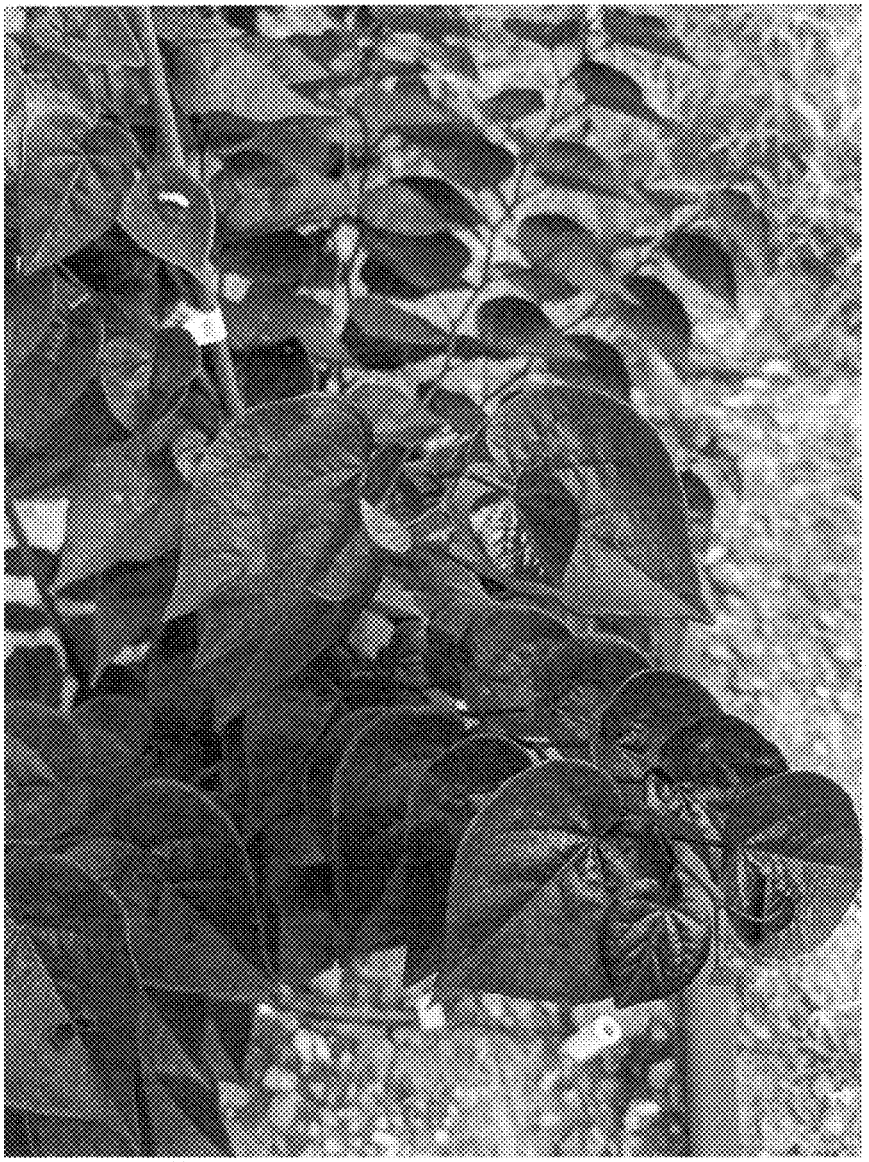
FIG. 2 illustrates a close-up view of the foliage of 'NC2017-6'

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values of the flowers were determined in spring 2020. Color values of the foliage were determined in summer 2020 under natural light conditions in Raleigh, N.C.

The following descriptions and measurements describe plants produced from chip budding and grown outside in Raleigh, N.C. Plants were approximately three years of age. Measurements and numerical values represent averages of typical plants.

Botanical classification: *Cercis canadensis* cultivar NC2017-6.

Parentage:

*Female parent.*—*Cercis* 'Ruby Falls', U.S. Plant Pat. No. 22,097.

*Male parent.*—*Cercis* 'Ace of Hearts', U.S. Plant Pat. No. 17,161.

Propagation:

*Type.*—Chip budding.

Plant description:

*Type.*—Deciduous perennial tree.

*Growth habit and general appearance.*—Moderately slow growing, highly branched and compact growth habit.

*Commercial crop time.*—Approximately 1.5 years from budding to finish as a 4 foot tree.

*Hardiness.*—USDA Zone 6b.

*Size.*—Height: Approximately 1.3 meters. Width: Approximately 88.1 cm.

*Trunk.*—Color: 201B. Texture: slightly rough. Diameter: Approximately 2.0 cm.

*Branches.*—Highly branched. Strength: Moderately strong. Diameter: Approximately 3.0 mm. Length: 20.5 cm. Internode length: 1.4 cm. Texture: Slightly rugose. Shape: round. Color of young stem: 59A. Color of mature stem: N200B. Lenticel: Approximately 35 lenticles on a length of a branch 2.0 cm long, tiny. Lenticel length: Less than 1.0 mm. Lenticel shape: circular to slightly elongate. Lenticel color: 197C.

Foliage description:

*General description.*—Type: Deciduous. Arrangement: Alternate.

*Leaves.*—Shape: Cordate. Apex: Acute. Base: Cordate. Margin: Entire. Number: Approximately 14 to 23 per stem. Length (to base of sinus): Approximately 3.8 cm. Length (to base of lobe): Approximately 4.6 cm. Sinus indentation: Approximately 0.9 cm. Width: Approximately 3.8 cm. Texture of upper and lower surfaces: Slightly rugose. Venation pattern: Reticulate. Color of upper surface of young foliage: N79B. Color of lower surface of young foliage: 59A. Color of upper surface of mature foliage: N77A. Color of lower surface of mature foliage: 59B with venation of 59D. Fragrance: None detected.

*Petiole.*—Length: Approximately 2.5 cm. Diameter: Approximately 1.0 mm. Texture: Smooth, glabrous. Color: N79B.

Flowering description:

*Flowering season.*—Flowers in early spring for about 2-3 weeks depending on weather conditions.

*General description.*—Form: Fasicle. Flower Arrangement: Sessile clusters. Symmetry: Bilateral symmetry. Type: Papilionaceous. Quantity per cluster: 6 per cluster on average. Flower length: 5.6 mm on average. Flower width across wings at anthesis: 4.2 mm on average. Flower depth (bottom of keel petals to top of wings): 3.2 mm on average. Fragrance: Absent.

*Bud just before opening.*—Shape: Slightly elongate. Diameter: Approximately 1.0 mm. Length: Approximately 1.0 mm. Color: 60A. Texture: Glabrous.

*Petals.*—Quantity: 5, unfused. Texture of upper and lower surfaces: Glabrous. Color of banner, wings, and keel base when first and fully open: 73A. Color of keel tip when first and fully open: 61B. Length of keel: Approximately 5.4 mm. Length of banner: Approximately 6.2 mm. Length of wing: Approximately 5.4 mm. Diameter of keel: Midsection is approximately 3.0 mm and base is less than 1.0 mm. Diameter of banner: Midsection is approximately 2.0 mm and base is less than 1.0 mm. Diameter of wing: Midsection is 2.0 mm and base is less than 1.0 mm. Apex shape: Rounded for keel, banner, and wing petals. Base: Narrow, stalked for keel, banner, and wing petals. Margin: Entire for keel, banner, and wing petals.

*Calyx.*—Shape: vase-shaped. Diameter: Approximately 2.0 mm at top of hypanthium. Length: Approximately 3.0 mm. Color of outer and inner surfaces: 59B. Texture of inner and outer surfaces: Glabrous.

*Sepals.*—Arrangement: Fused. Length: Approximately 2.0 mm. Diameter: Approximately 3.0 mm at tip and 1.0 mm at base. Color: 59B.

*Pedicel.*—Strength: Strong. Shape: Round. Length: Approximately 4.0 mm. Diameter: Less than 1.0 mm. Texture: Glabrous. Color: 60C.

*Reproductive organs*.—Androecium: Stamen quantity per flower: 10 on average, unfused and attached to apex of hypanthium. Stamen length: Less than 1.0 mm. Filament color: 65A. Anther shape: Round. Anther length: 4.0 mm. Anther width: Less than 1.0 mm. Anther color: 65A. Pollen amount: Sparse. Pollen color: 11B. Gynoecium: Pistil length: Approximately 4.4 mm on average. Pistil width: Less than 1.0 mm. Pistil texture: Glabrous. Stigma shape: Round. Stigma color: 59D. Stigma length: Less than 1.0 mm. Stigma width: Less than 1.0 mm. Style shape: Round. Style length: Less than 1.0 mm. Style width: Less than 1.0 mm. Style color: 59A. Ovary position: Superior. Ovary shape: Elongate. Ovary length: Less than 1.0 mm. Ovary width: Less than 1.0 mm. Ovary color: 59A.

*Seed production*.—None observed to date.

*Disease and pest resistance*.—Plants of the new *Cercis* have not been noted to be resistant to pathogens and pests common to *Cercis*.

We claim:

1. A new and distinct cultivar of *Cercis* plant named 'NC2017-6', substantially as herein illustrated and described.

* * * * *